United States Patent [19]

Kuo

[11] Patent Number: 5,312,830
[45] Date of Patent: May 17, 1994

[54] 3-CYCLOALKYL-PROP-2-ENAMIDES

[75] Inventor: Elizabeth A. Kuo, Swindon Wilts, England

[73] Assignee: Roussel-Uclaf, France

[21] Appl. No.: 944,830

[22] Filed: Sep. 14, 1992

[30] Foreign Application Priority Data

Sep. 17, 1991 [GB] United Kingdom ........... 9119874
Jul. 1, 1992 [GB] United Kingdom ........... 9213972

[51] Int. Cl.$^5$ ............... A61K 31/275; C07C 255/34
[52] U.S. Cl. .................... 514/464; 514/521;
546/270; 546/292; 549/438; 558/392; 558/393
[58] Field of Search ............ 558/392, 393; 514/521,
514/464; 549/438

[56] References Cited

U.S. PATENT DOCUMENTS

| | | | |
|---|---|---|---|
| 4,061,767 | 12/1977 | Ertel et al. | 558/392 X |
| 5,034,410 | 7/1991 | Sjogren et al. | 558/392 X |
| 5,066,657 | 11/1991 | Hayashi et al. | 558/393 X |
| 5,240,960 | 8/1993 | Hambleton et al. | 558/292 X |

Primary Examiner—Joseph Paul Brust
Attorney, Agent, or Firm—Bierman and Muserlian

[57] ABSTRACT

A compound selected from the group consisting of a compound of the formula

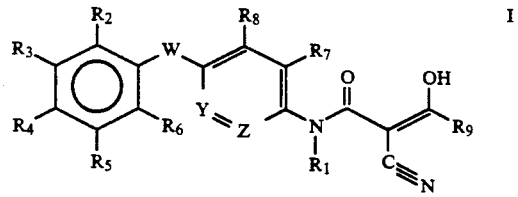

wherein $R_1$ is hydrogen or alkyl of 1 to 3 carbon atoms, W is selected from the group consisting of —O—, —S—, —SO— and —SO$_2$—, Z and Y are —CH— or one is —CH— and the other is —N—, $R_2$, $R_3$, $R_4$, $R_5$ and $R_6$ are individually selected from the group consisting of hydrogen, halogen, methoxy, methylthio, alkyl of 1 to 4 carbon atoms, —WCF$_3$, —CF$_3$, —NO$_2$, —CN—, —W—(CH$_2$)$_n$—CF$_3$, —W—(CF$_2$)$_n$—CF$_3$, —(CF$_2$)$_n$—CF$_3$ and —(CH$_2$)$_n$—CX$_3$, is an integer from 1 to 3, X is a halogen or $R_3$ and $R_4$ together are —O—(CH$_2$)—O— and $R_2$, $R_5$ and $R_6$ are as defined above, $R_7$ and $R_8$ are individually hydrogen or alkyl of 1 to 6 carbon atoms, $R_9$ is cycloalkyl of 3 to 6 carbon atoms and their non-toxic, pharmaceutically acceptable salts with bases.

12 Claims, No Drawings

3-CYCLOALKYL-PROP-2-ENAMIDES

OBJECTS OF THE INVENTION

It is an object of the invention to provide the novel compounds of formula I and a novel process and intermediates for their preparation.

It is another object of the invention to provide novel anti-inflammatory compositions and to a novel method of relieving inflammation in warm-blooded animals.

These and other objects and advantages of the invention will become obvious from the following detailed description.

THE INVENTION

The novel compounds of the invention are all tautomeric forms of a compound selected from the group consisting of a compound of the formula

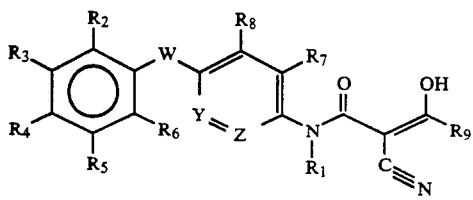

wherein $R_1$ is hydrogen or alkyl of 1 to 3 carbon atoms, W is selected from the group consisting of —O—, —S—, —SO— and —SO$_2$—, Z and Y are —CH— or one is —CH— and the other is —N—, $R_2$, $R_3$, $R_4$, $R_5$ and $R_6$ are individually selected from the group consisting of hydrogen, halogen, methoxy, methylthio, alkyl of 1 to 4 carbon atoms, —WCF$_3$, —CF$_3$, —NO$_2$, —CN, —W—(CH$_2$)$_n$—CF$_3$, —W—(CF$_2$)$_n$—CF$_3$, —(CF$_2$)$_n$—CF$_3$ and —(CH$_2$)$_n$—CX$_3$, n is an integer from 1 to 3, X is a halogen or $R_3$ and $R_4$ together are —O—(CH$_2$)—O— and $R_2$, $R_5$ and $R_6$ are as defined above, $R_7$ and $R_8$ are individually hydrogen or alkyl of 1 to 6 carbon atoms, $R_9$ is cycloalkyl of 3 to 6 carbon atoms and their non-toxic, pharmaceutically acceptable salts with bases.

Examples of alkyl of 1 to 4 carbon atoms are methyl, ethyl, isopropyl, n-propyl, n-butyl, isobutyl and tert.-butyl and examples of alkyl of 1 to 6 carbon atoms include besides these groups, linear or branched pentyl and hexyl. Cycloalkyl of 3 to 6 carbon atoms include cyclopropyl, cyclobutyl, cyclopentyl and cyclohexyl. Halogen includes fluorine, bromine, chlorine and iodine, preferably fluorine, chlorine and bromine.

Examples of suitable non-toxic, pharmaceutically acceptable bases are inorganic bases such as sodium hydroxide, potassium hydroxide, sodium carbonate, potassium carbonate or organic bases such as amines like ethanolamine or triethylamine.

Among the preferred compounds of formula I are those wherein $R_1$ is hydrogen or methyl, those wherein W is —O—, those wherein $R_2$, $R_3$, $R_4$, $R_6$ and $R_6$ are individually selected from the group consisting of hydrogen, fluorine, chlorine, bromine, iodine, —CH$_3$, —OCH$_3$, —OCF$_3$, —CF$_3$, —NO$_2$, —CN and —W—(CH$_2$)$_n$—CF$_3$ or $R_3$ and $R_4$ are —OCH$_2$O— and $R_2$, $R_5$ and $R_6$ are hydrogen, those wherein $R_7$ and $R_8$ are hydrogen and those wherein $R_9$ is cyclopropyl.

More preferred compounds are those wherein $R_1$ is hydrogen, W is —O—, $R_2$, $R_3$, $R_4$, $R_5$ and $R_6$ are individually selected from the group consisting of hydrogen, fluorine, chlorine, iodine and —NO$_2$ or $R_3$ and $R_4$ form —OCH$_2$O— and $R_2$, $R_5$ and $R_6$ are hydrogen, $R_7$ and $R_8$ are hydrogen and $R_9$ is cyclopropyl.

Specific preferred compounds are N-[4-(4'-chlorophenoxy)-phenyl]-2-cyano-3-cyclopropyl-3-hydroxy-prop-2-enamide; 2-cyano-3-cyclopropyl-3-hydroxy-N-[4-(4'-nitrophenoxy)-phenyl]-prop-2-enamide; 2-cyano-3-cyclopropyl-3-hydroxy-N-[4-(3',4'-methylenedioxy-phenoxy)-phenyl]-prop-2-enamide; 2-cyano-3-cyclopropyl-3-hydroxy-N-[4-(4'-fluorophenoxy)-phenyl]-prop-2-enamide;2-cyano-3-cyclopropyl-3-hydroxy-N-[4-(4'-iodophenoxy)-phenyl]-prop-2-enamide; and base addition salts thereof.

The novel process of the invention for the preparation of compounds of formula I comprises reacting a compound of the formula

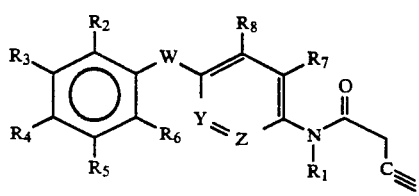

wherein $R_1$, $R_2$, $R_3$, $R_4$, $R_5$, $R_6$, $R_7$, $R_7$, W, Y and Z are as defined above with sodium hydride where appropriate in the presence of a catalyst such as imidazole and reacting the product thereby obtained with a compound of the formula

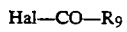

Hal—CO—R$_9$    V wherein Hal is halogen and $R_9$ has the above definition to obtain the corresponding compound of formula I.

The reaction between the compound of formula IV and sodium hydride is preferably effected in the presence of an anhydrous organic solvent such as tetrahydrofuran.

The compound of formula IV may, for example, be obtained by reacting a compound of the formula

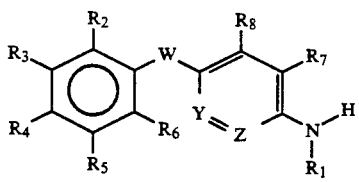

wherein $R_1$, $R_2$, $R_3$, $R_4$, $R_5$, $R_6$, $R_7$, $R_8$, W, Y and Z are as defined above with a compound of the formula

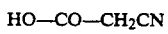

HO—CO—CH$_2$CN    III.

The reaction between the compounds of formulae II and III is preferably effected in the presence of phosphorous pentachloride in an anhydrous organic solvent such as tetrahydrofuran or dichloromethane.

The compounds of formula II when they are not already known may be prepared by reducing a compound of the formula

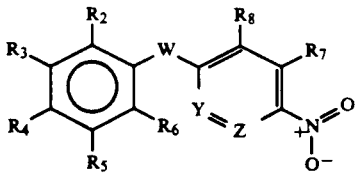

wherein $R_2$, $R_3$, $R_4$, $R_5$, $R_6$, $R_7$, $R_8$, W, Y and Z are as defined above. The reduction is preferably effected with hydrogen in the presence of a catalyst or with a mixture of iron filings and hydrochloric acid. Examples of such preparations are given in the examples.

The compounds of formula VI wherein $R_2$, $R_3$, $R_4$, $R_5$, $R_6$, $R_7$, $R_8$, Y and Z are as defined above and W is S, O or $SO_2$ may be prepared by reacting a compound of the formula

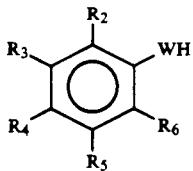

wherein W, $R_2$, $R_3$, $R_4$, $R_5$ and $R_6$ are as defined above with a compound of the formula

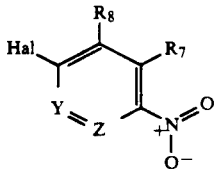

wherein Hal, $R_7$, $R_8$, Y and Z are as defined above.

The compounds of formula VI wherein $R_2$, $R_3$, $R_4$, $R_5$, $R_6$, $R_7$, $R_8$, Y and Z are as defined above and W is SO or $SO_2$ may be prepared by oxidizing the corresponding compound of formula VI Wherein W is sulfur.

The compounds of formula I are acidic in character and the base addition salts of the compounds of formula I can be advantageously prepared by reacting in approximately stoichiometric proportions an inorganic base or organic amine with the compound of formula I. The salts can be prepared without intermediate isolation of the corresponding acidic compound.

The novel anti-inflammatory compositions of the invention are comprised of an anti-inflammatorily effective amount of at least one compound of formula I and its basis salts and an inert pharmaceutical carrier. The compositions may be in the form of tablets, dragees, capsules, granules, suppositories or injectable solutions or suspensions.

Examples of suitable excipients are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

The compositions have a remarkable anti-inflammatory and immunological activity. They inhibit the inflammatory response caused by irritant agents and delayed hypersensitivity reactions, by hindering the activation of the immune cells by a specific antigen. They are useful in the treatment of rheumatoid arthritis and chronic inflammatory diseases of immune or non-immune origin, autoimmune diseases, diseases and conditions arising from transplanation, graft-versus-host diseases, and other immunologically mediated diseases.

The novel method of the invention for relieving inflammation in warm-blooded animals, including humans, comprises administering to warm-blooded animals an anti-inflammatorily effective amount of at least one compound of formula I and their basic, pharmaceutically acceptable salts. The compounds may be administered orally, rectally or parenterally and the usual daily dose is 0.0013 to 2.66 mg/kg depending on the condition treated, the specific compound and the method of administration.

The novel intermediates of the invention are the compounds of formula IV.

In the following examples, there are described several preferred embodiments to illustrate the invention. However, it is to be understood that the invention is not intended to be limited to the specific embodiments.

EXAMPLE 1

N-[4-(4'-chlorophenoxy)-phenyl]-2-cyano-3-cyclopropyl-3-hydroxy prop-2-enamide

STEP A: 4-(4'-chlorophenoxy)-nitrobenzene

A solution of 10.5 g (75.0 mmole) of 1-fluoro-4-nitrobenzene in 100 ml of dimethylsulfoxide and 9.64 g (75 mmole) of chlorophenol in 100 ml of DMSO was heated to 70° C. and maintained at this temperature for 4 hours. After allowing to cool to room temperature, 250 ml of water and then 250 ml of ethyl acetate were added slowly. The layers were separated and the organic layer was washed with 5×b 250 ml of water and 100 ml of sodium chloride, orange solid. Flash chromatography ($CH_2Cl_2$ eluent) yielded 18.34 g (98.0%) of the desired product as a yellow-orange solid.

STEP B: 4-(4'-chlorophenoxy) aniline

A suspension of 16.0 g (64.1 mmole) of 4-(4'-chlorophenoxy) nitrobenzene and 75% Pt, 161 mg of platinum oxide (641 μmole, 1 mole %) in 200 ml of ethanol was stirred vigorously under hydrogen until hydrogen uptake ceased (about 4 hours). The suspension was filtered through celite and the solution was evaporated to dryness to obtain 13.94 g (99.3%) of the desired product as a pale brown solid.

STEP C:
N-[4-(4'-chlorophenoxy)-phenyl]-2-cyano-ethanamide 8.06 g, (94.8 mmole, 1.5 equiv) of dry cyanoacetic acid were added in 4 to 5 portions over 30 minutes to a mechanically stirred suspension of 19.73 g, (94.8 mmole, 1.5 equiv) of phosphorous pentachloride in 150 ml of $CH_2Cl_2$. The solution was refluxed under a slow stream of nitrogen for 1 hour, before adding a solution of 13.68 g (63.2 mmole) of 4-(4'-chlorophenoxy) aniline in 150 ml of dichloromethane dropwise over 30 minutes. The suspension was mechanically stirred for 1.5 hours, then allowed to cool to room temperature. The suspension was stirred with 250 ml of water for 1 hour and after removal of the water, the suspension was stirred with 250 ml of saturated aqueous $NaHCO_3$ for 1 hour. Ethyl acetate was added to dissolve the solid and the layers were separated. The organic phase was washed with 100 ml of brine, dried over $MgSO_4$, filtered and evaporated to obtain 17.49 g (96.5%) of the desired product as a fawn powder.

STEP D:
N-[4-(4'-chlorophenoxy)-phenyl]-2-cyano-3-cyclo-propyl-3-hydroxy-prop-2-enamide A solution of 7.0 g, (24.4 mmole) of N-[4-(4'-chlorophenoxy)phenyl]-2-cyan ethanamide in 80 ml of tetrahydrofuran was added dropwise over 1 hour to a mechanically stirred suspension of 2.20 g (73.2 mmole, 3.0 equiv.) of sodium hydride (80% dispersion in oil in 5 ml of tetrahydrofuran. The grey-brown suspension was stirred at room temperature for 1.5 hours and a solution of 3.32 g (2.88 ml, 31.7 mmole) of cyclopropane carbonyl chloride in 10 ml of tetrahydrofuran was then added in a dropwise manner over 20 minutes. After stirring for a further 20 minutes, the brown solution was added slowly to a vigorously stirred mixture of 150 ml of 2M HCl and 350 ml of ice-water. The suspension was stirred for 10 minutes, then was filtered and dried in vacuo. Impurities were removed by stirring the product in 150 ml of diethyl ether for 30 minutes. The product was filtered, washed with 40° to 60° C. petroleum ether and dried in vacuo to obtain 5.51 g (63.6%) of the desired product as an off-white powder melting at 160.5° to 162.5° C.

Analysis: $C_{19}H_{15}ClN_2O_3$; molecular weight = 354.80

| | % C | % H | % Cl | % N | % O |
|---|---|---|---|---|---|
| Calculated: | 64.32 | 4.26 | 9.99 | 7.90 | 13.53 |
| Found: | 63.95 | 4.31 | 10.26 | 7.91 | 13.57 |

RMN CDCl3

1.11–1.24 (2H,m); 1.27–1.37 (2H,m); 2.09–2.19 (1H,m); 6.94 (2H, d+v, J=8.8); 7.00 (2H, d+v, J=8.8); 7.30 (2H, d+v, J=8.8); 7.44 (2H, d+v, J=8.8); 7.51 (1H, Br s) and 15.84 (1H,s).

IR Spectrum: cm$^{-1}$ 3272 (m), 2217 (m), 1544 (s), 1501 (s), 1482 (s), 1324 (m), 1350 (m), 1286 (m), 1258 (m), 1234 (s), 1196 (m), 1086 (m), 900 (m), 878 (m) and 823 (m).

The following compounds were prepared using the procedure of Example 1:

EXAMPLE 2
2-Cyano-3-cyclopropyl-3-hydroxy-(4'-phenoxyphenyl)-propen-2-amide melting at 142.0° C.

Analysis: $C_{19}H_{16}N_2O_3$; molecular weight = 320.35

| | % C | % H | % N | % O |
|---|---|---|---|---|
| Calculated: | 71.24 | 5.03 | 8.74 | 14.98 |
| Found: | 71.11 | 5.13 | 8.73 | |

EXAMPLE 3
2-Cyano-3-cyclopropyl-N-hydroxy-N-[4-(4'-nitrophenoxy)-phenyl]propen-2-amide Melting at 197.0° to 198.0° C.

Analysis: $C_{19}H_{15}N_3O_5$; molecular weight = 365.35

| | % C | % H | % N | % O |
|---|---|---|---|---|
| Calculated: | 62.46 | 4.14 | 11.50 | 21.90 |
| Found: | 62.32 | 4.23 | 11.44 | |

RMN (DMSO)

10.56 (1H,s); 8.30 (2H,d); 7.68 (2H,d); 7.23 (2H,d); 7.16 (2H,d); 2.22 (1H,m); 1.17 (4H,m).

IR Spectrum: cm$^{-1}$ 3380, 2220, 1590, 1550, 1505, 1425, 1350, 1260, 1235, 1195, 1170, 1115, 1015, 990.

EXAMPLE 4
2-cyano-3-cyclopropyl-3-hydroxy-N-[4-(3',4'-methylenedioxyphenoxy)phenyl]-prop-2-enamide melting at 150.5° to 151.5° C.

Analysis: $C_{20}H_{16}N_2O_5$; molecular weight = 364.36

| | % C | % H | % N | % O |
|---|---|---|---|---|
| Calculated: | 65.93 | 4.43 | 7.69 | 21.96 |
| Found: | 65.74 | 4.46 | 7.67 | 22.13 |

RMN (CDCl3):

1.09–1 21 (2H,m); 1.25–1.36 (2H,m); 2.09–2.20 (1H,m); 5.98 (2H,s); 6.49 (1H,AB q, J=8.0–2.4); 6.57 (1H,d, J=2.4); 6.76 (1H,d, J=8.2); 6.96 (2H, d+v, J=9.0); 7.38 (2H, d+v, J=8.8); 7.47 (1H, Br s) and 15.89 (1H,s).

IR Spectrum: cm$^{-1}$ 3250 (s), 2209 (s), 1574 (s), 1539 (s), 1500 (s), 1481 (s), 1240 (m), 1214 (s), 1170 (m), 1031 (m), 926 (m).

EXAMPLE 5
2-cyano-3-cyclopropyl-N-[4-(4'-fluoro-phenoxy)-phenyl]-3-hydroxy prop-2-enamide melting at 135.5° to 136.5° C.

Analysis: $C_{19}H_{15}FN_2O_3$; molecular weight = 338.34

| | % C | % H | % F | % N | % O |
|---|---|---|---|---|---|
| Calculated: | 67.45 | 4.47 | 5.62 | 8.28 | 14.19 |
| Found: | 67.25 | 4.53 | 5.65 | 8.24 | 14.33 |

RMN (CDCl3)

1.10–1.21 (2H,m); 1.27–1.36 (2H,m); 2.07–2.20 (1H,m); 6.93–7.09 (6H,m); 7.41 (2H, d+v, J=8.8); 7.48 (1H, Br s) and 15.85 (1H,s).

IR Spectrum: cm$^{-1}$ 3280 (m), 2220 (m), 1577 (s), 1541 (s), 1496 (s), 1422 (m), 1412 (m), 1352 (m), 1291 (m), 1257 (m), 1228 (m), 1211 (s), 1188 (m), 1160 (m), 992 (m), 899 (m), 879 (m), 849 (m), 824 (m), 814 (m), 764 (m).

EXAMPLE 6

2-cyano-3-cyclopropyl-3-hydroxy-N-[4-(4'-iodophenoxy)-phenyl]prop-2-enamide 2-cyano-3-cyclopropyl-3-hydroxy-N-[4-(4'-iodophenoxy)phenyl]-prop-2-enamide was prepared from 4-(4'-iodophenoxy) aniline (synthetised as described in Method A) as in Example 1 (Steps C and D) except that in Step C, the intermediate was added as a solid to the sodium hydride/THF solution and in Step D, the product was purified by stirring with methanol to obtain the desired product melting at 162.0° to 164.0° C.

| Analysis: $C_{19}H_{15}IN_2O_3$; molecular weight = 446.25 | | | | | |
|---|---|---|---|---|---|
| Calculated: | % C 51.14 | % H 3.39 | % I 28.44 | % N 6.28 | % O 10.76 |
| Found: | 51.00 | 3.43 | 28.42 | 6.30 | 10.85 |

RMN (CDCl₃)

1.10–1.37 (4H,m); 2.11–2.21 (1H,m); 6.77 (2H, d+v, J=9.0); 7.01 (2H, d+v, J=8.8); 7.44 (2H, d+v, J=9.0); 7.51 (1H,s); 7.62 (2H, d+v, J=8.8); 15.83 (1H,s).

IR Spectrum: cm⁻¹

3265 (m), 2212 (m), 1576 (s), 1530 (s), 1500 (s), 1477 (s), 1421 (m), 1406 (m), 1351 (m), 1272 (m), 1251 (m), 1233 (s), 1195 (m), 1163 (m), 1005 (m), 900 (m), 874 (m), 815 (m).

METHOD A

Preparation of 4-(4'-iodophenoxy) Aniline

A solution of 6.04 ml (68.4 mmole) of concentrated hydrochloric acid in 25 ml of water and 25 ml of ethanol was added in a dropwise manner over 50 minutes to a mechanically stirred refluxing suspension of 23.34 g (68.4 mmole) of 4-(4'-iodophenoxy) nitrobenzene and 11.46 g (205 mmole, 3.0 equiv) of iron filings in 150 ml of water and 150 ml of ethanol. After 1 hour, the mixture was allowed to cool to room temperature and was evaporated to about 200 ml volume. The mixture was made alkaline to a pH of about 11 using 10% aqueous sodium hydroxide solution before adding 200 ml of water and 250 ml of ethyl acetate. The aqueous fraction was extracted twice with 50 ml of ethyl acetate and the combined organic phase was washed twice with 125 ml of water and 50 ml of brine, dried over MgSO₄, filtered and evaporated to obtain 20.25 g of the desired product as a brown semi solid. Flash column chromatography (0–10% EtOAc/CH₂Cl₂ eluent) yielded 13.40 g (62.9%) of the product as pale brown crystals.

EXAMPLE 7

N-[[2-(4'-chlorophenoxy)-phenyl]-pyridin-5-yl]-2-cyano-3-cyclopropyl-3-hydroxy-prop-2-enamide N-[[2-(4'-chlorophenoxy)-phenyl]-pyridin-5-yl] 2-cyano-3-cyclopropyl-3-hydroxy-prop-2-enamide was prepared from 2-chloro 5-nitropyridine and 4-chlorophenol using the procedure of Example 1 with the modification described in Example 6 for Steps C and D. The product melted at 198.0° to 199° C.

| Analysis: $C_{18}H_{14}ClN_3O_3$; molecular weight = 355.78 | | | | | |
|---|---|---|---|---|---|
| Calculated: | % C 60.77 | % H 3.97 | % Cl 9.96 | % N 11.81 | % O 13.49 |
| Found: | 60.42 | 4.00 | 9.97 | 11.80 | 13.81 |

RMN (CDCl₃)

1.12–1.38 (4H,m); 2.07–2.22 (1H,m); 6.96 (1H,d,J=8.8); 7.08 (2H, d+v, J=8.8); 7.52 (1H, Br s); 7.92 (1H, dd, J=8.8-2.8); 8.21 (1H,d, J=2.8); 15.61 (1H,s).

IR Spectrum: cm⁻¹

3285 (m), 2218 (m), 1614 ()m), 1572 (m), 1542 (s), 1487 (m), 1469 (s), 1343 (m), 1259 (s), 1228 (s), 1203 (m), 1083 (m), 991 (m), 983 (m).

EXAMPLE 8

2-cyano-3-cyclopropyl-3-hydroxy-N-[4-(4'-trifluoromethylphenoxy)phenyl]-prop-2-enamide was obtained in a yield of 71% and melted at 150.5° to 152.0° C.

| Analysis: $C_{20}H_{15}F_3N_2O_3$; molecular weight = 388.35 | | | | | |
|---|---|---|---|---|---|
| Calculated: | % C 61.86 | % H 3.89 | % F 14.68 | % N 7.21 | % O 12.36 |
| Found: | 61.82 | 3.96 | 14.55 | 7.19 | 12.48 |

RMN (CDCl₃)

1.11–1.38 (4H,m); 2.09–2.24 (1H,m); 7.05 (2H, d, J=9); 7.06 (2H,d+v, J=9); 7.49 (2H, d+v, J=9); 7.53 (1H,s); 7.59 (2H,d, J=9); 15.7 (1H,s).

IR Spectrum: cm⁻¹

3280 (m), 2218 (s), 1609 (s), 1577 (s), 1551 (s), 1502 (s), 1421 (m), 1335 (s), 1313 (s), 1293 (m), 1258 (s), 1232 (s), 1198 (m), 1170 (m), 1114 (m), 1103 (s), 1068 (s), 1012 (m), 897 (m), 878 (m), 850 (m), 835 (s).

EXAMPLE 9

2-cyano-3-cyclopropyl-N-[4-(3',4'-dimethoxyphenoxy)-phenyl]-3-hydroxy-prop-2-enamide was obtained in a yield of 79% and melted at 154° to 156.° C.

| Analysis: $C_{21}H_{20}N_2O_5$; molecular weight = 380.40 | | | | |
|---|---|---|---|---|
| Calculated: | % C 66.31 | % H 5.30 | % N 7.36 | % O 21.03 |
| Found: | 66.09 | 5.50 | 7.16 | 21.25 |

RMN (CDCl₃)

1.15 (2H,m); 1.31 (2H,m); 2.15 (1H,m); 3.84 (3H,s); 3.89 (3H,s); 6.56 (1H, dd, J=2.8-8.6); 6.64 (1H,d, J=2.4); 6.83 (1H,d J=8.6); 6.96 (2H,d, J=8.8); 7.39 (2H,d J=9.0); 7.54 (1H,s); 15.39 (1H,s).

IR Spectrum: cm⁻¹

380 (m), 2212 (m), 1540 (s), 1500 (s), 1220 (s).

EXAMPLE 10

2-cyano-3-cyclopropyl-N-[4-(4'-chloro-3'-methylphenoxy)-phenyl]-3-hydroxy-prop-2-enamide was obtained in a yield of 75% and melted at 154.0° C. to 156° C.

| Analysis: C₂₀H₁₇ClN₂O₃; molecular weight = 368.82 | | | | | |
|---|---|---|---|---|---|
| Calculated: | % C 65.13 | % H 4.65 | % Cl 9.61 | % N 7.60 | % O 13.01 |
| Found: | 65.18 | 4.79 | 9.65 | 7.42 | 12.96 |

RMN (CDCl₃)

1.10-1.36 (4H,m); 2.09-2.34 (1H,m); 2.34 (3H,s); 6.78 (1H, dd, J=8.6-2.8); 6.88 (1H,d, J=2.8); 6.99 (2H,d, J=8.8); 7.28 (1H,d, J=8.6); 7.42 (2H,d, J=8.8); 7.51 (1H,s); 15.6 (1H,s).

IR Spectrum: cm⁻¹

3264 (m), 2200 (m), 1600 (m), 1570 (m), 1563 (m), 1535 (s), 1500 (s), 1468 (s), 1408 (m), 1340 (m), 1292 (m), 1265 (m), 1220 (m), 1198 (m), 885 (m); 843 (m), 798 (m).

EXAMPLE 11

2-cyano-3-cyclopropyl-N-[4-(4'-chloro-2'-methylphenoxy)-phenyl]-3-hydroxy prop-2-enamide was obtained in a yield of 60% and melting at 128.0° to 129.0° C.

RMN (CDCl₃)

1.10-1.36 (4H,m); 2.08-2.16 (1H,m); 2.21 (3H,s); 6.83 (1H,d, J-8.8); 6.89 (2H,d, J=9); 7.13 (1H,dd, J=8.6-2.8); 7.24 (1H,d, J=2.4); 7.39 (2H,d J=8.8); 7.48 (1H,s); 15.87 (1H,s).

IR Spectrum: cm⁻¹

270 (m), 2180 (m), 1595 (m), 1570 (s), 1535 (s), 1490 (s), 1465 (s), 1400 (m), 1335 (m), 1215 (s), 1195 (s), 1165 (s), 880 (m), 855 (m), 815 (m), 800 (m).

EXAMPLE 12

2-cyano-3-cyclopropyl-N-[4-(4'-chlorophenoxy)-3-methylphenyl]-3-hydroxy-prop-2-enamide was obtained in a yield of 66% and melted at 24.0° to 125.0° C.

| Analysis: C₂₀H₁₇ClN₂O₃; molecular weight = 368.82 | | | | | |
|---|---|---|---|---|---|
| Calculated: | % C 65.13 | % H 4.65 | % Cl 9.61 | % N 7.60 | % O 13.01 |
| Found: | 64.99 | 4.75 | 9.63 | 7.58 | 13.05 |

RMN (CDCl₃)

1.13-1.34 (4H,m); 2.1-2.22 (1H,m); 2.22 (3H,s); 6.83 (2H,d, J=9.2); 6.89 (1H,d, J=8.8); 7.23-7.30 (3H,m); 7.36 (1H,d, J=2.6); 7.47 (1H,s); 15.84 (1H,s).

IR Spectrum: cm⁻¹

3270 (m), 2180 (m), 1600 (m), 1520 (s), 1470 (s), 1400 (s), 1330 (m), 1240 (m), 1200 (s), 1180 (m), 1070 (m), 995 (m), 880 (m), 830 (m), 790 (m).

EXAMPLE 13

2-cyano-3-cyclopropyl-N-[4-(4'-chlorophenoxy)-2-methylphenyl]-3-hydroxy-prop-2-enamide was obtained in a yield of 66% and melted at 144.0° to 145.0° C.

| Analysis: C₂₀H₁₇ClN₂O₃; molecular weight = 368.82 | | | | | |
|---|---|---|---|---|---|
| Calculated: | % C 65.13 | % H 4.65 | % Cl 9.61 | % N 7.60 | % O 13.01 |
| Found: | 65.07 | 4.71 | 9.67 | 7.48 | 13.07 |

RMN (CDCl₃)

1.13-1.34 (4H,m); 2.1-2.22 (1H,m); 2.27 (3H,s); 6.84-6.97 (4H,m); 7.28-7.54 (4H,m); 15.86 (1H,s).

IR Spectrum: cm⁻¹

3260 (m), 2215 (m), 1580 (s), 1540 (s), 1480 (s), 1415 (s), 1350 (m), 1290 (s), 1255 (m), 1225 (s), 1200 (s), 1165 (m), 1080 (m), 1000 (m), 950 (m), 900 (m), 875 (m), 825 (s), 810 (s), 655 (m).

EXAMPLE 14

2-cyano-3-cyclopropyl-N-[4-(4'-bromophenoxy)-phenyl]-3-hydroxy-prop-2-enamide was obtained in a yield of 74% and melted at 154.0° to 155.0° C.

| Analysis: C₁₉H₁₅BrN₂O₃; molecular weight = 399.25 | | | | | |
|---|---|---|---|---|---|
| Calculated: | % C 57.16 | % H 3.79 | % Br 20.01 | % N 7.02 | % O 12.02 |
| Found: | 57.20 | 3.90 | 19.74 | 6.95 | 12.21 |

RMN (CDCl₃)

1.10-1.36 (4H,m); 2.09-2.21 (1H,m); 6.90 (2H,d, J=10.4); 7.01 (2H, d, J=10); 7.4-7.48 (4H,m); 7.56 (1H,s); 15.85 (1H,s).

IR Spectrum: cm⁻¹

3260 (m), 2250 (m), 1600 (m), 1570 (s), 1540 (s), 1500 (s), 1480 (s), 1420 (m), 1350 (m), 1270 (m), 1255 (s), 1230 (s), 1190 (m), 1160 (m), 1000 (m), 875 (m), 820 (s).

EXAMPLE 15

2-cyano-3-cyclopropyl-N-[4-(4'-cyanophenoxy)-phenyl]-3-hydroxy-prop-2-enamide was obtained in a yield of 87% and melted at 180.0° to 182.0° C.

| Analysis: $C_{20}H_{15}N_3O_3$; molecular weight = 345.36 | | | | | | | | |
|---|---|---|---|---|---|---|---|---|
| Calculated: | % C | 69.56 | % H | 4.38 | % N | 12.17 | % O | 13.90 |
| Found: | | 69.83 | | 4.56 | | 11.99 | | 13.62 |

RMN (CDCl₃)

1.12–1.38 (4H,m); 2.1–2.22 (1H,m); 7.02 (2H,d, J=9); 7.08 (2H,d, J=8.8); 7.49–7.65 (5H,m); 15.76 (1H,s).

IR Spectrum: cm⁻¹

3260 (m), 2210 (m), 1595 (s), 1570 (m), 1540 (s), 1495 (s), 1415 (m), 1350 (m), 1285 (m), 1255 (s), 1230 (s), 1190 (m), 1165 (m), 875 (m), 830 (m).

EXAMPLE 16

2-cyano-3-cyclopropyl 3-hydroxy-N-[4-(4'-trifluoromethoxyphenoxy) phenyl]-prop-2-enamide was obtained in a yield of 65% and melted at 126.0° to 127.0° C.

| Analysis: $C_{20}H_{15}F_3N_2O_4$; molecular weight = 404.35 | | | | | | | | | | |
|---|---|---|---|---|---|---|---|---|---|---|
| Calculated: | % C | 59.41 | % H | 3.74 | % F | 14.10 | % N | 6.93 | % O | 15.83 |
| Found: | | 59.31 | | 3.79 | | 14.14 | | 6.89 | | 15.87 |

RMN (CDCl₃)

1.15–1.33 (4H,m); 2.11–2.19 (1H,m); 6.99 (2H,d, J=3.94); 7.03 (2H,d, J=3.78); 7.19 (2H,d); 7.45 (2H,d, J=8.94); 7.54 (1H,s); 15.86 (1H,s).

IR Spectrum: cm⁻¹

3320 (m), 2190 (m), 1595 (m), 1575 (m), 1535 (s), 1480 (s), 1400 (m), 1340 (m), 1250 (s), 1235 (s), 1220 (s), 1205 (m), 1180 (s), 1150 (s), 880 (m), 825 (m).

EXAMPLE 17

2-cyano-3-cyclopropyl-N-[4-(4'-t-butylphenoxy)-phenyl]-3-hydroxy-prop-2-enamide was obtained in a yield of 39% and melted at 125.0° to 126.0° C.

| Analysis: $C_{23}H_{24}N_2O_3$; molecular weight = 376.46 | | | | | | | | |
|---|---|---|---|---|---|---|---|---|
| Calculated: | % C | 73.38 | % H | 6.43 | % N | 7.44 | % O | 12.75 |
| Found: | | 73.13 | | 6.64 | | 7.14 | | 13.09 |

RMN (CDCl₃)

1.10–1.46 (13H,m); 2.11–2.19 (1H,s); 6.94 (2H,d, J=8.60); 7.00 (2H,d, J=9.0); 7.36 (2H,d, J=9.0); 7.40 (2H,d, J=9.0); 7.52 (1H,s); 5.92 (1H,s).

IR Spectrum: cm⁻¹

340 (m), 3280 (m), 2960 (m), 2860 (m), 2200 (s), 1580 (s), 1545 (s), 1495 (s), 1410 (s), 1350 (s), 1310 (m), 1285 (m), 1245 (s), 220 (s), 1170 (m), 1105 (m), 1055 (m), 1005 (m), 890 (m), 825 (m).

EXAMPLE 18

2-cyano-3-cyclopropyl-3-hydroxy-N-[4-(4'-methylphenoxy)-phenyl]prop-2-enamide was obtained in a yield of 65% and melted at 146.0° to 147.0° C.

| Analysis: $C_{20}H_{18}N_2O_3$; molecular weight = 334.38 | | | | | | | | |
|---|---|---|---|---|---|---|---|---|
| Calculated: | % C | 71.84 | % H | 5.43 | % N | 8.38 | % O | 14.35 |
| Found: | | 71.93 | | 5.54 | | 8.30 | | 14.23 |

RMN (CDCl₃)

1.09–1.35 (4H,m); 2.08–2.21 (1H,m); 2.34 (3H,s); 6.91 (2H,d, J=8.6); 6.97 (2H,d, J=9.0); 7.15 (2H,d, J=8.4); 7.39 (2H,d, J=8.8); 7.51 (1H,s); 15.92 (1H,s).

IR Spectrum: cm⁻¹

3260 (m), 2210 (m), 1595 (s), 1580 (s), 1530 (s), 1495 (s), 1420 (s), 1345 (s), 1305 (m), 1250 (s), 1225 (s), 1165 (m), 985 (m), 895 (m), 875 (m), 820 (m), 685 (m).

EXAMPLE 19

2-cyano-3-cyclopropyl-3-hydroxy-N-[4-(4'-methoxyphenoxy)-phenyl]-prop-2-enamide was obtained in a yield of 57% and melted at 139.0° to 140° C.

RMN CDCl₃

1.10–1.36 (4H,m); 2.11–2.19 (1H,m); 6.87–7.01 (6H,m); 7.38 (2H,d, J=9.0); 7.53 (1H,s); 15.94 (1H,s).

IR Spectrum: cm⁻¹

3280 (s), 2200 (s), 1610 (m); 1590 (m), 1560 (s), 1520 (s), 1490 (s), 1460 (m), 1435 (m), 1410 (m), 1340 (m), 1240 (s), 1210 (s), 1170 (m), 1020 (m), 885 (m), 830 (m), 815 (m).

EXAMPLE 20

2-cyano-3-cyclobutyl-n-[4-(4'-fluorophenoxy)-phenyl]-3-hydroxy-prop-2-enamide was obtained in a yield of 81% and melted at 143.0° to 144.0° C.

| Analysis: $C_{20}H_{17}FN_2O_3$; molecular weight = 352.37 | | | | | | | | | | |
|---|---|---|---|---|---|---|---|---|---|---|
| Calculated: | % C | 68.17 | % H | 4.86 | % F | 5.39 | % N | 7.95 | % O | 13.62 |
| Found: | | 68.05 | | 4.97 | | 5.40 | | 7.90 | | 13.68 |

RMN (CDCl₃)

1.91–2.49 (6H,m); 3.65 (1H,q, J=8.4); 6.93–7.11 (6H,m); 7.41 (2H, d, J=9.0); 7.53 (1H,s); 15.82 (1H,s).

IR Spectrum: cm$^{-1}$ 3270 (s), 2980 (m), 2940 (m), 2220 (m), 1610 (s), 1575 (s), 1545 (s), 1490 (s), 1440 (m), 1415 (m), 1385 (m), 1325 (m), 1240 (m), 1205 (s), 820 (s).

EXAMPLE 21

2-cyano-3-cyclopentyl-N-[4-(4'-fluorophenoxy)-phenyl]-3-hydroxy-prop-2-enamide was obtained in a yield of 44% and melted at 119.0° to 120° C.

| Analysis: $C_{21}H_{19}FN_2O_3$; molecular weight = 366.40 | | | | | |
|---|---|---|---|---|---|
| Calculated: | % C 68.84 | % H 5.23 | % F 5.19 | % N 7.65 | % O 13.10 |
| Found: | 68.86 | 5.36 | 5.17 | 7.66 | 12.95 |

RMN (CDCl$_3$)

1.59-2.05 (8H,m); 317-3.24 (1H,m); 6.93-7.13 (6H,m); 7.41 (2H, d, J=9.0); 7.56 (1H,s); 15.76 (1H,s).

IR Spectrum: cm$^{-1}$ 3280 (s), 2950 (m), 2870 (m), 2205 (s), 1590 (s), 1535 (s), 1495 (s), 1420 (m), 1390 (m), 1350 (m), 1300 (m), 1250 (s), 1215 (s), 1190 (s), 1165 (m), 1095 (m), 995 (m), 850 (m), 825 (s), 805 (m).

EXAMPLE 22

2-cyano-3-cyclopropyl-N-[4'-(chlorophenylthio)-phenyl]-3-hydroxy prop-2-enamide was obtained in a yield of 81% and melted at 147.5° to 148.0° C.

| Analysis: $C_{19}H_{15}ClN_2O_2S$; molecular weight = 370.86 | | | | | |
|---|---|---|---|---|---|
| Calculated: | % C 61.54 | % H 4.08 | % Cl 9.56 | % N 7.55 | % S 8.65 |
| Found: | 61.51 | 4.23 | 9.57 | 7.48 | 8.57 |

RMN (CDCl$_3$)

1.10-1.22 (2H,m); 1.24-1.36 (2H,m); 2.09-2.19 (1H,m); 7.17-7.27 (4H,m); 7.35 (2H,d, J=8.76); 7.46 (2H,d, J=8.72); 7.54 (1H,s); 15.73 (1H,s).

IR Spectrum: cm$^{-1}$ 3466 (m), (3394 (m), 3058 (m), 2222 (m), 1900 (m), 1668 (m), 1622 (m), 1578 (s), 1530 (s), 1489 (m), 1469 (m), 1453 (m), 1402 (m), 1375 (m), 1345 (m), 1330 (m), 1310 (m), 1260 (m), 1229 (m), 1116 (m), 1100 (m), 1084 (m), 1006 (m), 983 (m).

EXAMPLE 23

2-cyano-3-cyclopropyl-N-[4'(chlorophenyl-sulfonyl)-phenyl]-3-hydroxy-prop-2-enamide was obtained in a yield of 85% and melted at 210.0° to 212.0° C.

| Analysis: $C_{19}H_{15}ClN_2O_4S$; molecular weight = 402.86 | | | | | |
|---|---|---|---|---|---|
| Calculated: | % C 56.65 | % H 3.75 | % Cl 8.80 | % N 6.95 | % S 7.96 |
| Found: | 56.52 | 3.85 | 8.75 | 6.96 | 7.86 |

RMN (CDCl$_3$)

1.14-1.27 (2H,m);1 1.31-1.39 (2H,m); 2.08-2.21 (1H,m); 7.48 (2H,d, J=8.8); 7.67 (2H,d, J=8.8); 7.75 (1H,s); 7.87 (2H,d, J=8.6); 7.92 (2H,d, J=8.6); 15.42 (1H,s).

IR Spectrum: cm$^{-1}$ 3286 (m), 2216 (m), 1575 (s), 1569 (s), 1533 (s), 1496 (m), 1404 (m), 1350 (m), 1317 (m), 1310 (m), 1262 (m), 1150 (s), 1104 (m), 1087 (m), 993 (m), 837 (m), 757 (s), 707 (m), 653 (m).

EXAMPLE 24

Tablets were prepared containing 20 mg of the compound of Example 1 or 4 and sufficient excipient of lactose, starch, talc and magnesium stearate for a tablet of 150 mg.

PHARMACOLOGICAL DATA

Test 1

Carrageenan Rat Paw Oedema (PO-R)

One hour after the oral administration of the test compounds at a dose of 50 mg/kg or control vehicle to groups of rats [n=6-12, male CFHB, weight range 160-280 mg], 1 mg of carrageenan dissolved in 0.2 ml of saline was injected into the right hind foot pad. Contralateral paws received control saline injection and the paw oedema responses were assessed three hours later.

Test 2

Delayed-type Hypersensitivity Mouse Paw Oedema (DTH-M)

Groups of mice [n=8-10, male CD-1, weight range 25 to 30 g] were sensitized by subcutaneous injection of 1 mg of methylated bovine serum albumin (MBSA) in 0.2 ml volumes of saline/Freund's complete adjuvant (FCA) emulsion. Negative control group received injections of saline/FCA emulsion. DTH paw oedema responses were assessed twenty-four hours after the right hind foot pad was challenged with 0.1 mg of MBSA in 0.05 ml volumes of saline on day seven after sensitization. Contralateral paws received control saline injections. The test compounds or control vehicles were orally administered daily on days four, five, six and twice on day seven, one hour before and six hours after MBSA challenge.

Test 3

Delayed-type Hypersensitivity Rat Paw Oedem (DTH-R)

Groups of rats [n=8-12, male CFHB, weight range 160 to 180 mg] were sensitized by the subcutaneous tail base injection with 0.1 ml volumes of FCA. Negative control groups received an injection of Freund's incomplete adjuvant. DTH paw oedema responses were assessed twenty-four hours after the right hind foot pad challenge with 0.4 mg of Mycobacterium tuberculosis extract antigen in 0.2 ml volumes of saline on day seven after sensitization. Contralateral paws received control saline injections. The test compounds were orally administered daily on days four, five, six and twice on day seven, one hour before and six hours after antigenic challenge. The results of these tests are given in the following Table. Doses are given in units of mg/kg p.o.

TABLE

| Example | Test 1 | Test 2 | Test 3 |
|---|---|---|---|
| 1 | 25 | 63 (30) | 31 (10) |
| 2 | 20 | 9 (100) | 6 (50) |
| 3 | 14 | 66 (100) | 22 (50) |
| 4 | 23 | 104 (100) | 44 (50) |
| 5 | 25 | 18 (30) | 59 (10) |
| 6 | 24 | 86 (30) | 38 (10) |
| 7 | 18 | 16 (30) | 12 (10) |
| 8 | 29 (50) | −17 (30) | 39 (10) |
| 9 | 20 (50) | −18 (100) | 27 (50) |
| 10 | 24 (50) | 2 (100) | 47 (50) |
| 11 | 20 (50) | 11 (100) | 66 (50) |
| 12 | 2 (50) | 53 (30) | 50 (10) |
| 13 | 3 (10) | 49 (30) | 13 (10) |
| 14 | 14 (10) | 42 (30) | 38 (10) |
| 15 | 10 (10) | 61 (100) | 29 (10) |
| 16 | 15 (10) | 21 (10) | 64 (10) |
| 17 | 20 (50) | 25 (100) | 43 (50) |
| 18 | 16 (50) | 47 (100) | 30 (50) |
| 19 | 7 (50) | 12 (100) | −1 (50) |
| 20 | 14 (50) | −5 (30) | 31 (50) |
| 21 | 3 (50) | 28 (30) | 22 (50) |
| 22 | 17 (50) | 62 (100) | 25 (50) |
| 23 | 15 (50) | 11 (100) | −13 (50) |

Various modifications of the compounds and method of the invention may be made without departing from the spirit or scope thereof. It is to be understood that the invention is intended to be limited only as defined in the appended claims.

What is claimed is:

1. A compound selected from the group consisting of a compound of the formula

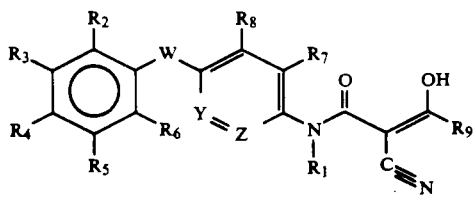

wherein $R_1$ is hydrogen or alkyl of 1 to 3 carbon atoms, W is selected from the group consisting of —O—, —S—, —SO— and —SO$_2$, Z and Y are —CH—, $R_2$, $R_3$, $R_4$, $R_5$ and $R_6$ are individually selected from the group consisting of hydrogen, halogen, methoxy, methylthio, alkyl of 1 to 4 carbon atoms, —WCF$_3$, —CF$_3$, —NO$_2$, —CN, —W—(CH$_2$)$_n$—CF$_3$, —W—(CF$_2$)$_n$—CF$_3$, —(CF$_2$)$_n$—CF$_3$ and —(CH$_2$)$_n$—CX$_3$, n is an integer from 1 to 3, X is a halogen or $R_3$ and $R_4$ together are —O—(CH$_2$)—O— and $R_2$, $R_5$ and $R_6$ are as defined above, $R_7$ and $R_8$ are individually hydrogen or alkyl of 1 to 6 carbon atoms, $R_9$ is cycloalkyl of 3 to 6 carbon atoms and their non-toxic, pharmaceutically acceptable salts with bases.

2. A compound of claim 1 wherein $R_1$ is hydrogen or methyl, W is —O—, $R_2$, $R_3$, $R_4$, $R_5$ and $R_6$ are individually selected from the group consisting of hydrogen, fluorine, chlorine, bromine, iodine, —CH$_3$, —OCH$_3$, —OCF$_3$, —CF$_3$, —NO$_2$, —CN and —W(CH$_2$)$_n$—CF$_3$ or $R_3$ and $R_4$ together are —OCH$_2$O— and $R_2$, $R_5$ and $R_6$ are hydrogen, $R_7$ and $R_8$ are hydrogen and $R_9$ is cyclopropyl.

3. A compound of claim 1 wherein $R_1$ is hydrogen, W is —O—, $R_2$, $R_3$, $R_4$, $R_5$ and $R_6$ are individually selected from the group consisting of hydrogen, fluorine, chlorine, iodine and —NO$_2$ or $R_3$ and $R_4$ together form —OCH$_2$O— and $R_2$, $R_5$ and $R_6$ are hydrogen, $R_7$ and $R_8$ are hydrogen and $R_9$ is cyclopropyl.

4. A compound of claim 1 selected from the group consisting of N-[4-(4'-chlorophenoxy)-phenyl]-2-cyano-3-cyclopropyl-3-hydroxy-prop-2-enamide; 2-cyano-3-cyclopropyl-3-hydroxy-N-[4-(4'-nitrophenoxy)-phenyl]-prop-2-enamide; 2-cyano-3-cyclopropyl-3-hydroxy-N-[4-(3',4'-methylene-dioxyphenoxy)-phenyl]-prop-2-enamide; 2-cyano-3-cyclopropyl-3-hydroxy-N-[4-(4'-fluorophenoxy)-phenyl]prop-2-enamide; 2-cyano-3-cyclopropyl-3-hydroxy-N-[4-(4'-iodophenoxy)-phenyl]-prop-2-enamide; and their non-toxic, pharmaceutically acceptable base addition salts.

5. An anti-inflammatory composition comprising an anti-inflammatorily effective amount of at least one compound of claim 1 and an inert pharmaceutical carrier.

6. A composition of claim 5 wherein $R_1$ is hydrogen or methyl, W is —O—, $R_2$, $R_3$, $R_4$, $R_5$ and $R_6$ are individually selected from the group consisting of hydrogen, fluorine, chlorine, bromine, iodine, —CH$_3$, —OCH$_3$, —OCF$_3$, —CF$_3$, —NO$_2$, —CN and —W—(CH$_2$)$_n$—CF$_3$ or $R_3$ and $R_4$ together are —OCH$_2$O— and $R_2$, $R_5$ and $R_6$ are hydrogen, $R_7$ and $R_8$ are hydrogen and $R_9$ is cyclopropyl.

7. A composition of claim 5 wherein $R_1$ is hydrogen, W is —O—, $R_2$, $R_3$, $R_4$, $R_5$ and $R_6$ are individually selected from the group consisting of hydrogen, fluorine, chlorine, iodine and —NO$_2$ or $R_3$ and $R_4$ together form —OCH$_2$O— and $R_2$, $R_5$ and $R_6$ are hydrogen, $R_7$ and $R_8$ are hydrogen and $R_9$ is cyclopropyl.

8. A composition of claim 5 wherein the active compound is N-[4-(4'-chlorophenoxy)-phenyl]-2-cyano-3-cyclopropyl-3-hydroxy-prop-2-enamide; 2-cyano-3-cyclopropyl-3-hydroxy-N-[4-(4'-nitrophenoxy)-phenyl]-prop-2-enamide; 2-cyano-3-cyclopropyl-3-hydroxy-N-[4-(3',4'-methylene-dioxyphenoxy)-phenyl]-prop-2-enamide; 2-cyano-3-cyclopropyl-3-hydroxy-N-[4-(4'-fluorophenoxy)-phenyl]prop-2-enamide; 2-cyano-3-cyclopropyl-3-hydroxy-N-[4-(4'-iodophenoxy)-phenyl]-prop-2-enamide; and their non-toxic, pharmaceutically acceptable base addition salts.

9. A method of relieving inflammation in warm-blooded animals comprising administering to warm-blooded animals an anti-inflammatorily effective amount of at least one compound of claim 1.

10. A method of claim 9 wherein $R_1$ is hydrogen or methyl, W is —O—, $R_2$, $R_3$, $R_4$, $R_5$ and $R_6$ are individually selected from the group consisting of hydrogen, fluorine, chlorine, bromine, iodine, —CH$_3$, —OCH$_3$, —OCF$_3$, —CF$_3$ NO$_2$, CN and —W—(CH$_2$)$_n$—CF$_3$ or $R_3$ and $R_4$ together are —OCH$_2$O— and $R_2$, $R_5$ and $R_6$ are hydrogen, $R_7$ and $R_8$ are hydrogen and $R_9$ is cyclopropyl.

11. A method of claim 9 wherein $R_1$ is hydrogen, W is —O—, $R_2$, $R_3$, $R_4$, $R_5$ and $R_6$ are individually selected from the group consisting of hydrogen, fluorine, chlorine, iodine and —NO$_2$ or R$_3$ and R$_4$ together form —OCH$_2$O— and R$_2$, R$_5$ and R$_6$ are hydrogen, R$_7$ and R$_8$ are hydrogen and R$_9$ is cyclopropyl.

12. A method of claim 9 wherein the active compound is N-[4-(4'-chlorophenoxy)-phenyl]-2-cyano-3-cyclopropyl-3-hydroxy-prop-2-enamide; 2-cyano-3-cyclopropyl-3-hydroxy-N-[4-(4'-nitrophenoxy)-phenyl]-prop-2-enamide; 2-cyano-3-cyclopropyl-3-hydroxy N-[4-(3',4'-methylene-dioxyphenoxy)-phenyl]-prop-2-enamide; 2-cyano-3-cyclopropyl-3-hydroxy-N-[4-(4'-fluorophenoxy)phenyl]-prop-2-enamide; 2-cyano-3-cyclopropyl-3-hydroxy-N-[4-(4'-iodophenoxy)-phenyl]-prop-2-enamide; and their non-toxic, pharmaceutically acceptable base addition salts.

* * * * *